United States Patent [19]

Kirsch

[11] Patent Number: Plant 6,173

[45] Date of Patent: May 10, 1988

[54] LILY PLANT NAMED TINY

[75] Inventor: Ted T. Kirsch, Myrtle Point, Oreg.

[73] Assignee: Melridge Inc., Gresham, Oreg.

[21] Appl. No.: 861,242

[22] Filed: May 8, 1986

[51] Int. Cl.[4] ..... A01H 5/00

[52] U.S. Cl. ..... Plt./68

[58] Field of Search ..... Plt./68

*Primary Examiner*— Robert E. Bagwill

*Attorney, Agent, or Firm*—Charles W. Rummler; W. Dennis Drehkoff

[57] ABSTRACT

A new and distinct lily cultivar of the Oriental hybrid type characterized by its short stature and silhouette and a compact raceme of large, light pink flowers of good form and substance, with abundant foliage, the plant also having a sturdy and vigorous growth habit and being capable of forced out-of-season production with reliable performance.

1 Drawing Sheet

BACKGROUND OF THE INVENTION

This new variety of lily plant originated as a seedling of unknown parentage discovered by me at my nursey in Arcata, Calif., in June 1979. The large, richly colored flowers in combination with the short plant stature prompted me to propagate this seedling for further evaluation, particularly because it appeared appropriate for culture as a pot plant cultivar. Propagation of this seedling was done by me and under my direction at Arcata, Calif., and successive generations produced by bulb scale propagation, natural propagation from bulblets and division, and tissue culture propagation originating from bulb scales have demonstrated that the novel and distinctive characteristics of this new lily variety hold true under asexual propagation from generation to generation and appear to be fixed.

I have found that bulbs which have been dug at the proper stage of maturity and have been properly precooled can be forced into flower out-of-season with excellent performance, even during periods of relatively low light.

DESCRIPTION OF THE DRAWING

My new variety of lily plant is illustrated by the accompanying photographic drawing which, in the upper view, shows the distinctive short silhouette of this plant as a potted cultivar, and the lower view is a close-up face view of a typical bloom to show its attractive bowl-shaped formation, the color rendition of both views being as nearly true as can be reasonably obtained by conventional photographic procedures.

DESCRIPTION OF THE NEW VARIETY

The following is a detailed description of this new variety of Oriental hybrid lily based upon observations made on greenhouse grown plants at Sandy, Oreg., in the spring of 1985 and with nomenclature according to The International Lily Register (The Royal Horticultural Society, London, 1969) and with color designations according to The R.H.S. Colour Chart published in 1966.

THE PLANT

Origin: Seedling.
Parentage: Unknown.
Classification:

*Botanic.*—Hybrid Lilium Cultivar; Division VII-B of The Horticultural Classification of Lilies (The Royal Horticultural Society).

*Commercial.*—Oriental Hybrid Lily.

Form: Single stem, erect and bushy.

Height: About 30 to 50 cm.

Growth: Vigorous, sturdy and compact with good strength.

Foliage:

*Quantity.*—Abundant.

*Leaf size.*—Ranging from about 8 cm. long and 2 cm. wide at the top of the stem to about 4 cm. long and 1.5 cm. wide at the bottom.

*Leaf shape.*—Broad lanceolate and somewhat reflexing.

*Texture.*—Leathery.

*Aspect.*—Glossy.

*Color.*—Dark green (chlorophyll pigmentation overlaid with anthocyanin).

Bulb:

*Size.*—Vary up to 30 cm. in circumference depending upon age.

*Color.*—White, with flushes of soft pink or yellow which deepen as the bulbs become larger or are exposed to light.

THE BUD

Form: Ovate and generally urn-shaped with obtuse apex.

Size: Averages about 10 to 12 cm. long and 10 cm. in circumference, depending upon light and nutritional levels.

Opening rate: The bud open slowly in response to morning light; the buds open successively from the lowermost to the upper most in the typical manner of Lilium.

Color: Medium magenta-rose, 63C-D, just before opening, shading to a softer tone at the tips of the buds.

Peduncle:

*Length.*—About 2 to 3 cm. The peduncle may elongate under low light conditions or when bulbs have been improperly stored prior to forcing.

*Color: Dark green.*

THE FLOWER

Blooming habit: The flowers bloom once and profusely in midseason, usually late in July, under field conditions at Arcata, Calif. This plant will flower in 95 to 110 days in greenhouse when properly forced from appropriately precooled bulbs.

Size: Large; averaging about 18 to 20 cm. in diameter with recurving tepals presenting a bowl shape about 13 to 15 cm. wide and about 4 to 5 cm. deep.

Borne: As a compact raceme with each pedicel having one bud. Stems from typical commercial bulbs bear an average of four to eight flowers.

Shape: Bowl-shaped, with broad overlapping tepals, slightly recurved.

Tepalage:

*Number.*—Six.

*Arrangement.*—Hexagonal.

*Form.*—Generally ovate with the inner tepals averaging about 4 cm. wide and slightly overlapping and the outer tepals averaging about 2.5 cm. wide.

*Color.*—The basic color is red-purple, 62D, with a deeper band of 62B about 1 cm. wide along the tepal midrib. The outer tepals curl slightly inward along the margins and do not reflex, but they may twist slightly in the clockwise direction when viewed from the top. The papallae occur on each side of the nectaries and are 63B in color. The nectaries are green with a yellow margin about 2 to 4 mm. wide at each side.

*Color change.*—The color fades slightly and becomes more brown as the flower ages or in intense light and heat. Under cool conditions, the color is richer and is retained longer.

*Tepal longevity.*—The tepals stay on the stem about two to three weeks.

Pedicel:

*Length.*—About 5 to 10 cm. in an irregular pattern. There are no secondary buds.

Disease resistance: The flower and plant are adequately resistant to disease as observed at Arcata, Calif., and at Sandy, Oreg.

Fragrance: The fragrance is heavy and sweet.

Lasting quality: The flower is long lasting, both on field grown plants and on forced potted cultivars.

REPRODUCTIVE ORGANS

Stamens:

*Number.*—Six.

*Arrangement.*—Typical of genus Lilium.

Anthers:

*Color.*—16A-B.

Filaments:

*Length.*—About 7 to 8 cm.

*Color.*—Light green.

Pistil: One per flower.

Style:

*Color.*—Light green to white, sometimes slightly pink.

Stigma:

*Size.*—Large.

*Color.*—Light purple-grey.

Ovary: Typical of genus Lilium.

I claim:

1. A new and distinct variety of Oriental hybrid lily, substantially as herein shown and described, characterized by its short stature and silhouette and its moderately large, outwardly facing, richly colored flowers of good substance and form; by its vigorous growth habit and relatively short height; and by its ability for forcing out-of-season to produce reliable pot plant cultivars.

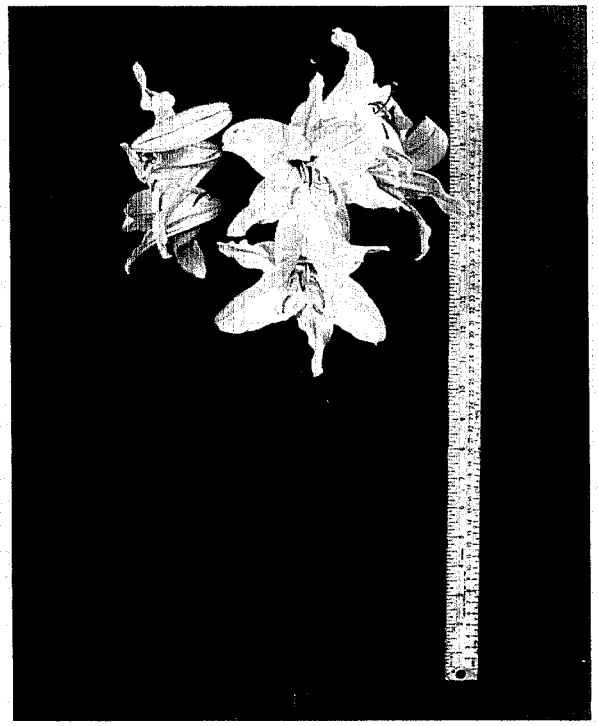
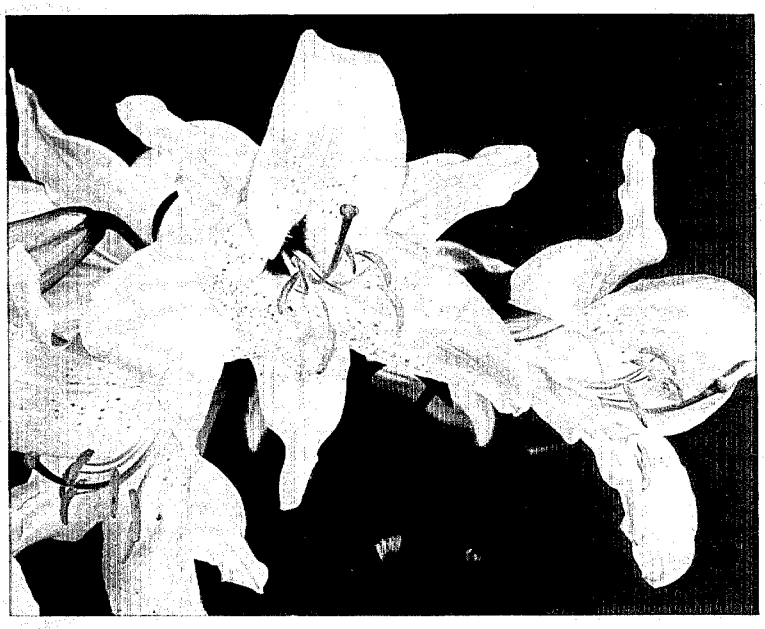

* * * * *